(12) United States Patent
Burns

(10) Patent No.: US 9,020,173 B2
(45) Date of Patent: Apr. 28, 2015

(54) METHOD AND APPARATUS FOR HARVESTING ENERGY IN A HEARING ASSISTANCE DEVICE

(71) Applicant: Starkey Laboratories, Inc., Eden Prairie, MN (US)

(72) Inventor: Thomas Howard Burns, St. Louis Park, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 13/897,161

(22) Filed: May 17, 2013

(65) Prior Publication Data

US 2013/0308807 A1 Nov. 21, 2013

Related U.S. Application Data

(60) Provisional application No. 61/648,200, filed on May 17, 2012.

(51) Int. Cl.
*H04R 25/00* (2006.01)
*A61N 1/36* (2006.01)

(52) U.S. Cl.
CPC ............ *H04R 25/50* (2013.01); *A61N 1/36032* (2013.01); *H04R 25/00* (2013.01); *H04R 2201/003* (2013.01); *H04R 2460/03* (2013.01)

(58) Field of Classification Search
CPC ...... H04R 25/00; H04R 25/30; H04R 25/305; H04R 25/60; H04R 25/602; H04R 25/604; H04R 25/65; H04R 11/00; H04R 11/02; H04R 11/06; H04R 11/14; H04R 2225/31; H04R 2225/33; H04R 2460/03; H04R 2201/003
USPC .................. 381/312, 314, 321–323; 324/244, 324/248–249; 365/157
See application file for complete search history.

(56) References Cited

U.S. PATENT DOCUMENTS

| | | | | |
|---|---|---|---|---|
| 7,970,161 | B2 * | 6/2011 | van Halteren | 381/398 |
| 8,343,790 | B2 * | 1/2013 | Lutz et al. | 438/51 |
| 2010/0032001 | A1 * | 2/2010 | Brantner | 136/244 |
| 2010/0217099 | A1 * | 8/2010 | LeBoeuf et al. | 600/301 |

OTHER PUBLICATIONS

Finkel et al., Magnetoelastic/piezoelectric laminated structures for tunable remote contactless magnetic sensing and energy harvesting, Feb. 17, 2009, AIP Publishing, Applied Physics Letters 94.*

* cited by examiner

*Primary Examiner* — Ahmad F Matar
*Assistant Examiner* — Sabrina Diaz
(74) *Attorney, Agent, or Firm* — Schwegman Lundberg & Woessner, P.A.

(57) ABSTRACT

The disclosure relates to the use of a MEMS magnetometer or an array of MEMS magnetometers as energy harvesting sensor(s) in a hearing assistance device. The MEMS magnetometer(s) can be located within the existing geometry of a typical balanced-armature receiver currently used in hearing assistance devices.

18 Claims, 3 Drawing Sheets

METHOD AND APPARATUS FOR HARVESTING ENERGY IN A HEARING ASSISTANCE DEVICE

RELATED APPLICATION(S)

The present application claims the benefit of priority under 35 U.S.C. §119(e) to U.S. Provisional Application No. 61/648,200 filed on May 17, 2012, which is incorporated herein by reference in its entirety.

FIELD OF THE INVENTION

The present subject matter relates generally to hearing assistance devices, and in particular to improved methods and devices for energy efficiency.

BACKGROUND

Hearing aids are electronic instruments worn in or around the ear that compensate for hearing losses by specially amplifying sound. Hearing aids use transducer and electro-mechanical components which are connected via wires to the hearing aid circuitry. In addition to transducers, modern hearing assistance devices incorporate A/D converters, DAC's, signal processors, memory for processing the audio signals, and wireless communication systems. The components frequently include multiple housings or shells that are connected to assemble the hearing aid.

In a hearing assistance device, electrical current consumption and battery life are important aspects to the device's performance and acceptance in the marketplace. Longer battery life may allow additional hardware functionality or algorithm capability. There is a desire, therefore, to develop and integrate technologies that could increase battery life or increase the available electrical current. Energy harvesting is one technology that can meet this desire. It would be advantageous to integrate this technology in a small form factor within the hearing assistance device.

DETAILED DESCRIPTION

Figure 1:
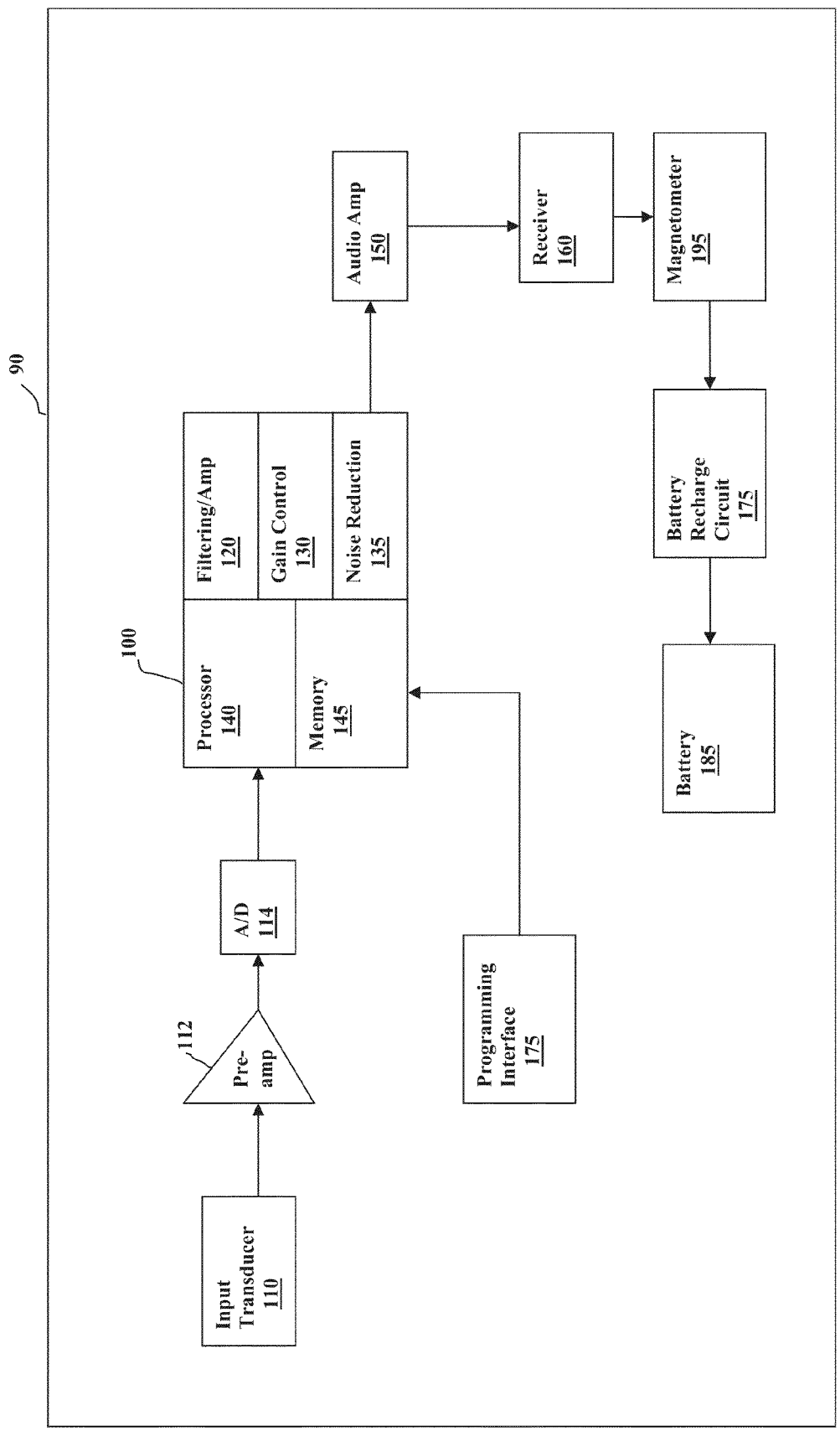
FIG. 1 illustrates components of an example hearing assistance device.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Disclosed herein, among other things, are methods and apparatus for hearing assistance devices. A hearing assistance device includes a housing and hearing assistance electronics. The device also includes a receiver configured to convert an electrical signal from the hearing assistance electronics to an acoustic signal. A sound outlet may be configured to transmit the acoustic signal from the receiver to the hearing assistance device, and an interface component may be configured to connect the sound outlet to the receiver. A damping element may be configured to connect the sound outlet to the hearing assistance device housing.

The present subject matter relates to the use of a MEMS (micro-electromechanical systems) magnetometer or an array of MEMS magnetometers as energy harvesting sensor(s) in a hearing assistance device. In general, a magnetometer is sensitive enough to detect relatively weak magnetic fields, and for this reason it has been used as a compass to detect the earth's magnetic field. A MEMS magnetometer can provide this functionality in the micro-structure of a silicon wafer using conventional foundry processes. Although an AC MEMS magnetometer may consume a small amount of electrical current to power an active internal circuit or sensor element, it may be configured to operate linearly within very large magnetic fields while drawing the same amount of electrical power, thereby behaving as an amplifier. This amplification responds not only to the magnetic field, but also to any vibrational energy since the silicon micro-structure of the sensing element contains a mechanical resonance that can be tuned over a wide range of frequencies.

The MEMS magnetometer(s) can be located within the existing geometry of a typical balanced-armature receiver currently used in hearing assistance devices. As such, the magnetometer(s) can produce an electrical output signal that derives from both the magnetic field and the motion due to vibration within the balanced armature receiver. The magnetometer is, therefore, responsive to two sources of energy; namely, mechanical and magnetic, and its output electrical signal is the superposition of the individual outputs for each energy source.

The MEMS magnetometer may be fabricated from standard silicon-on-insulator (SOI) processes so that the overall package is amenable to the form factor of hearing assistance devices and, more specifically, to the balanced armature receivers used in hearing assistance devices. The mechanical resonance frequency of the sensing element in the MEMS magnetometer can be designed to coincide with the mechanical resonance frequency of the armature inside the balanced armature receiver, thereby yielding maximum energy coupling. The electrical current in the charge pump of the magnetometer circuitry can be adjusted to fine-tune the electro-mechanical resonance frequency of the MEMS magnetometer, thereby allowing the system efficiency to be adjusted depending on the operating conditions and input electrical signal of the balanced armature receiver. In general, the magnetometer sensor itself consumes very little electrical power, thereby allowing higher efficiencies. The input and output electrical impedances of the MEMS magnetometer can be varied substantially by constructing multiple series or parallel magnetometers in the MEMS SOI architecture, thereby improving the electrical coupling and efficiency of the ancillary circuitry used in the harvesting stage of the system.

The electronic circuitry of a hearing aid is contained within a housing that is commonly either placed in the external ear canal or behind the ear. Transducers for converting sound to an electrical signal and vice-versa may be integrated into the housing or external to it. The basic components of an exemplary hearing aid are shown in FIG. 1. A battery 185 is contained within the housing 90 and supplies power to the electronic circuitry. A microphone or input transducer 110 receives sound waves from the environment and converts the sound into an input signal. After amplification by pre-amplifier 112, the signal is sampled and digitized by A/D converter 114. Other embodiments may incorporate an input transducer that produces a digital output directly. The device's signal processing circuitry 100 processes the digitized input signal IS into an analog output signal OS in a manner that compensates for the patient's hearing deficit. The output signal OS is then passed to an audio amplifier 150 that drives a receiver or output transducer 160 for converting the output signal into an audio output. In the embodiment illustrated in FIG. 1, the signal processing circuitry 100 includes a programmable controller made up of a processor 140 and associated memory 145 for storing executable code and data. The overall operation of the device is determined by the programming of the controller, which programming may be modified via a programming interface 210. The programming interface 175 allows user input of data to a parameter modifying area of the memory 145 so that parameters affecting device operation may be changed. The programming interface 175 may allow communication with a variety of devices for configuring the hearing aid such as industry standard programmers, wireless devices, or belt-worn appliances. Also shown in FIG. 1 is a MEMS magnetometer 195 that is connected to the receiver 160 for harvesting magnetic and/or vibrational energy produced during operation of the receiver. The magnetometer produces an amplified electrical signal that may be used to recharge the battery 185 via a battery recharge circuit 190. The operating parameters of the magnetometer may be adjusted by the programming interface as described above.

Figure 2:
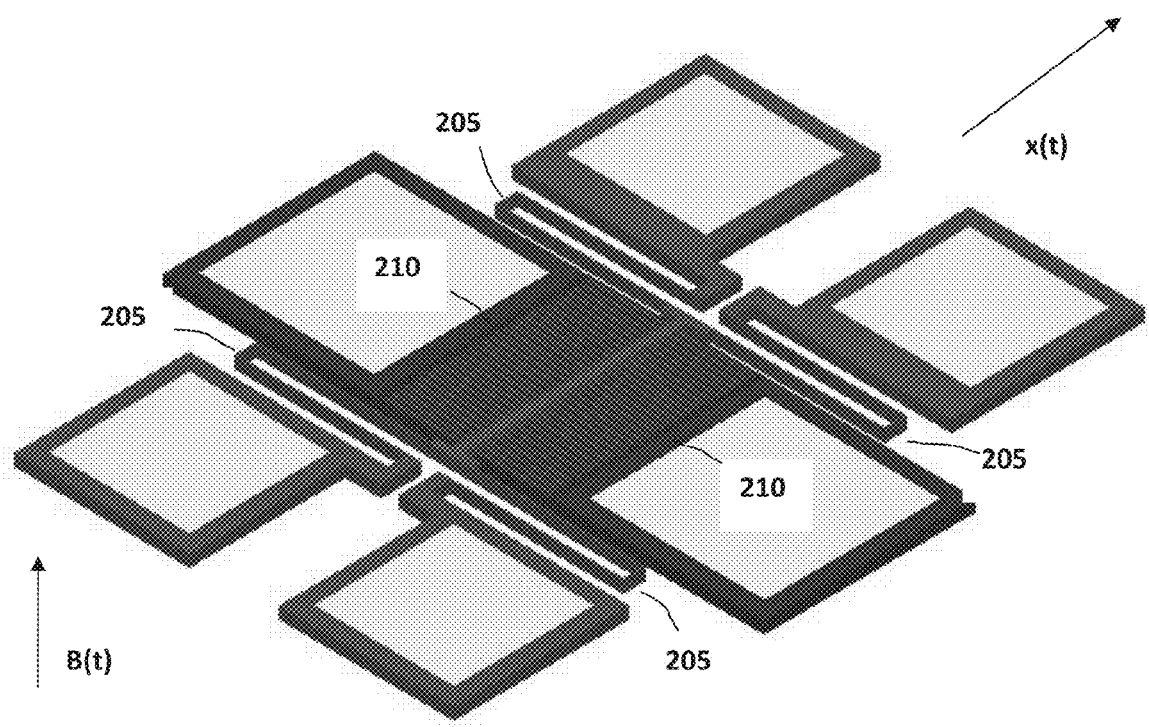
FIG. 2 illustrates an example MEMS magnetometer

The MEMS magnetometer may be fabricated with standard silicon-on-insulator (SOI) processes and foundry techniques. FIG. 2 illustrates an example MEMS magnetometer 200. The magnetometer array shown in FIG. 2 is an SOI crab-leg (leaf spring) MEMS device that is sensitive to both a magnetic B field and mechanical vibration. An out-of-plane magnetic field B(t) produces an in-plane Lorentz force x(t) that is modulated at the device's mechanical resonance frequency using an AC current passing through the flexures 205. The magnetometer is a resonant force sensor, which detects the displacement resulting from the Lorentz force on the current-carrying flexures 205 due to the magnetic field. Symmetric parallel capacitor plates 210 are provided for parametric excitation. In order to harvest energy, the magnetometer is placed inside a balanced armature receiver. A typical balanced armature receiver used in hearing aids typically generates a B-field of around 0.2T and a mechanical force of around 50 mN from which the MEMS magnetometer produces an output current that can be harvested. The fact that the electrical impedance of a MEMS magnetometer is much lower than typical piezo energy harvesting sensors provides for efficient harvesting, and the device may be fabricated in parallel/series to yield a range of electrical impedances.

Figure 3:
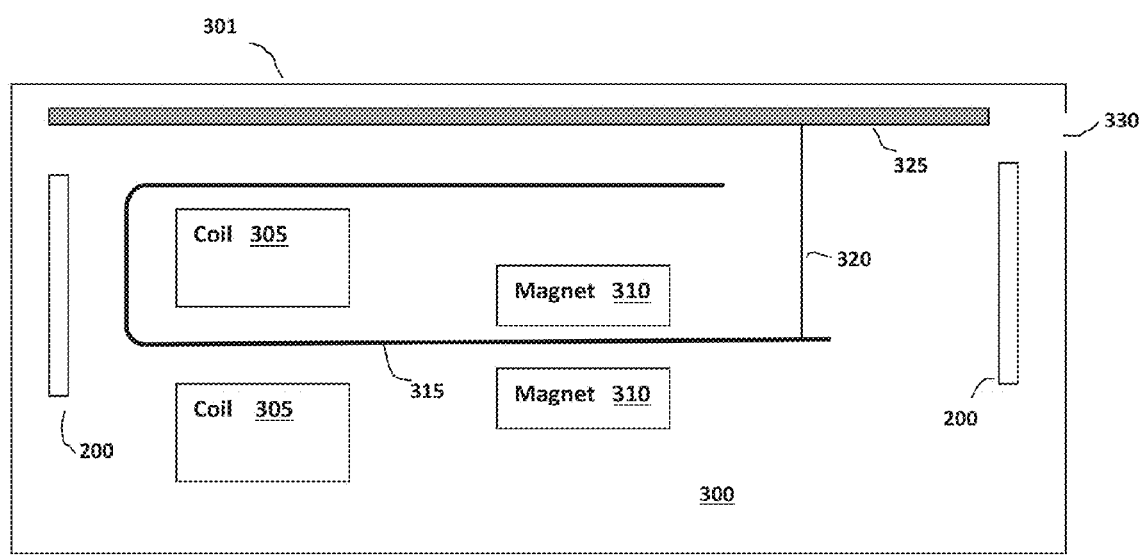
FIG. 3 illustrates a cross-section of an example balanced armature receiver.

One or more MEMS magnetometer(s) may be placed within a balanced-armature receiver for the purpose of harvesting magnetic and/or vibrational energy. A cross section of a typical balanced armature receiver 300 is illustrated in FIG. 3, together with example internal positions for the magnetometer arrays. The components of the receiver are contained within a housing 301. The coil 305 receives electronic signals from the audio amplifier and injects magnetic flux into the armature 315. The changing magnetic flux in the armature causes it to vibrate due to the magnetic field produced by magnets 310. The vibration of the armature is coupled to a membrane 325 by a drive pin 320. The resulting movement of the membrane pressures the air above the membrane, creating sound that is let out through a sound outlet 330. Magnetometers 200 are shown in this embodiment as positioned on both sides of the armature as to receive magnetic flux and produce an amplified electrical signal in response thereto. Receivers in hearing assistance devices usually have free real estate on the solder pad PCB (printed circuit board) surface which lies internal to the receiver. The SOI magnetometer may be integrated onto the same PCB used for the solder pads, and combined with the receiver solder pads. Mechanical coupling of the magnetometer to the receiver enables harvesting of vibrational energy produced by the receiver.

In one embodiment, a hearing assistance device, comprises: an input transducer for receiving sound and producing an input signal; electronic circuitry for amplifying the input signal to produce an output signal; a balanced armature receiver configured to convert the output signal from the electronic circuitry to sound; and, a MEMS magnetometer coupled to the receiver for harvesting magnetic energy produced by the receiver. The MEMS magnetometer may be mechanically coupled to the receiver to harvest vibrational energy produced by the receiver. The magnetometer may be fabricated by a silicon-on-insulator (SOI) process. The magnetometer may integrated onto a printed circuit board (PCB) internal to the receiver and may be integrated onto solder pads of the PCB. The mechanical resonance frequency of the magnetometer may be configured to coincide with the mechanical resonance frequency of the armature of the balanced armature receiver. The device may further comprise a programming interface for adjusting the electrical current in a charge pump of the magnetometer. The device may further comprise a battery for supplying power to the device, and the magnetometer may be configured to recharge the battery with energy harvested from the receiver. The device of may comprise multiple magnetometers connected in series or connected in parallel.

In one embodiment, a method for operating a hearing assistance device, comprises: receiving sound and producing an input signal; amplifying the input signal to produce an output signal; converting the output signal from the electronic circuitry to sound with a balanced armature receiver; and, harvesting magnetic energy produced by the receiver with a MEMS magnetometer coupled to the receiver. The MEMS magnetometer may be mechanically coupled to the receiver to harvest vibrational energy produced by the receiver. The magnetometer may be fabricated by a silicon-on-insulator (SOI) process. The magnetometer may be integrated onto a printed circuit board (PCB) internal to the receiver and may be integrated onto solder pads of the PCB. The method may further comprise configuring the mechanical resonance frequency of the magnetometer to coincide with the mechanical resonance frequency of the armature of the balanced armature receiver. The method may further comprise adjusting the electrical current in a charge pump of the magnetometer via a programming interface. The method may further comprise recharging a battery with energy harvested from the receiver. The method may further comprise harvesting energy using multiple magnetometers connected in series or connected in parallel.

It is understood that variations in configurations and combinations of components may be employed without departing from the scope of the present subject matter. Hearing assistance devices typically include an enclosure or housing, a microphone, hearing assistance device electronics including processing electronics, and a speaker or receiver. The examples set forth herein are intended to be demonstrative and not a limiting or exhaustive depiction of variations.

The present subject matter can be used for a variety of hearing assistance devices, including but not limited to, cochlear implant type hearing devices, hearing aids, such as behind-the-ear (BTE), in-the-ear (ITE), in-the-canal (ITC), or completely-in-the-canal (CIC) type hearing aids. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the user. Such devices are also known as receiver-in-the-canal (RIC) or receiver-in-the-ear (RITE) hearing instruments. It is understood that other hearing assistance devices not expressly stated herein may fall within the scope of the present subject matter.

This application is intended to cover adaptations or variations of the present subject matter. It is to be understood that the above description is intended to be illustrative, and not restrictive. The subject matter has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A hearing assistance device, comprising:
   an input transducer for receiving sound and producing an input signal;
   electronic circuitry for amplifying the input signal to produce an output signal;
   a balanced armature receiver configured to convert the output signal from the electronic circuitry to sound; and,
   a MEMS magnetometer coupled to the receiver for harvesting magnetic energy produced by the receiver and mechanically coupled to the receiver to harvest vibrational energy produced by the receiver.

2. The device of claim 1 wherein the magnetometer is fabricated by a silicon-on-insulator (SOI) process.

3. The device of claim 2 wherein the magnetometer is integrated onto a printed circuit board (PCB) internal to the receiver.

4. The device of claim 3 wherein the magnetometer is integrated onto solder pads of the PCB.

5. The device of claim 1 wherein the mechanical resonance frequency of the magnetometer is configured to coincide with the mechanical resonance frequency of the armature of the balanced armature receiver.

6. The device of claim 1 further comprising a programming interface for adjusting the electrical current in a charge pump of the magnetometer.

7. The device of claim 1 further comprising a battery for supplying power to the device and wherein the magnetometer is configured to recharge the battery with energy harvested from the receiver.

8. The device of claim 1 further comprising multiple magnetometers connected in series.

9. The device of claim 1 further comprising multiple magnetometers connected in parallel.

10. A method for operating a hearing assistance device, comprising:
    receiving sound and producing an input signal;
    amplifying the input signal to produce an output signal;
    converting the output signal from electronic circuitry to sound with a balanced armature receiver; and,
    harvesting magnetic energy produced by the receiver with a MEMS magnetometer coupled to the receiver and wherein the MEMS magnetometer is mechanically coupled to the receiver to harvest vibrational energy produced by the receiver.

11. The method of claim 10 wherein the magnetometer is fabricated by a silicon-on-insulator (SOI) process.

12. The method of claim 11 wherein the magnetometer is integrated onto a printed circuit board (PCB) internal to the receiver.

13. The method of claim 12 wherein the magnetometer is integrated onto solder pads of the PCB.

14. The method of claim 10 further comprising configuring the mechanical resonance frequency of the magnetometer to coincide with the mechanical resonance frequency of the armature of the balanced armature receiver.

15. The method of claim 10 further comprising adjusting the electrical current in a charge pump of the magnetometer via a programming interface.

16. The method of claim 10 further comprising recharging a battery with energy harvested from the receiver.

17. The method of claim 10 further comprising harvesting energy using multiple magnetometers connected in series.

18. The method of claim 10 further comprising harvesting energy using multiple magnetometers connected in parallel.

* * * * *